US008778695B2

(12) United States Patent
Caprioli

(10) Patent No.: US 8,778,695 B2
(45) Date of Patent: *Jul. 15, 2014

(54) METHODS AND APPARATUSES FOR ANALYZING BIOLOGICAL SAMPLES BY MASS SPECTROMETRY

(75) Inventor: Richard Caprioli, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 1736 days.

This patent is subject to a terminal disclaimer.

(21) Appl. No.: 10/880,750

(22) Filed: Jun. 29, 2004

(65) Prior Publication Data

US 2005/0029444 A1 Feb. 10, 2005

Related U.S. Application Data

(63) Continuation of application No. 10/178,067, filed on Jun. 21, 2002, now Pat. No. 6,756,586.

(60) Provisional application No. 60/329,719, filed on Oct. 15, 2001.

(51) Int. Cl.
*G01N 24/00* (2006.01)

(52) U.S. Cl.
USPC .............................................. 436/173; 436/86

(58) Field of Classification Search
None
See application file for complete search history.

(56) References Cited

U.S. PATENT DOCUMENTS

| 4,338,811 | A | 7/1982 | Miyagi et al. | 73/23.1 |
|---|---|---|---|---|
| 5,241,569 | A | 8/1993 | Fleming | 376/159 |
| 5,272,338 | A | 12/1993 | Winograd et al. | 250/309 |
| 5,372,719 | A | 12/1994 | Afeyan et al. | 210/502.1 |
| 5,453,199 | A | 9/1995 | Afeyan et al. | 210/638 |
| 5,569,915 | A | 10/1996 | Purser et al. | 250/281 |
| 5,594,243 | A | 1/1997 | Weinberger et al. | 250/288 |
| 5,607,859 | A | 3/1997 | Biemann et al. | 439/173 |
| 5,808,300 | A | 9/1998 | Caprioli | 250/288 |
| 5,827,190 | A | 10/1998 | Palcic et al. | 600/476 |
| 6,063,621 | A | 5/2000 | Deeley et al. | 453/330 |
| 6,197,599 | B1 | 3/2001 | Chin et al. | 436/518 |
| 6,225,047 | B1 | 5/2001 | Hutchens et al. | 435/5 |
| 6,254,834 | B1 | 7/2001 | Anderson et al. | 422/102 |
| 6,414,306 | B1 | 7/2002 | Mayer-Posner et al. | 250/288 |

FOREIGN PATENT DOCUMENTS

| WO | WO 97/38433 | 10/1997 |
|---|---|---|
| WO | WO 00/11208 | 3/2000 |
| WO | WO 01/36977 | 5/2001 |

OTHER PUBLICATIONS

Paweletz et al. "Rapid protein display profiling of cancer progression directly from human tissue using a protein biochip", Drug Dev. Res., Jan. 2000, v. 49, pp. 34-42.*
Reyzer et al. "MALDI Mass Spectrometry for Direct Tissue Analysis: A New Tool for Biomarker Discovery", J. Proteom. Res., 2005, v.4, pp. 1138-1142.*

(Continued)

*Primary Examiner* — Yelena G Gakh
(74) *Attorney, Agent, or Firm* — Parker Highlander PLLC

(57) ABSTRACT

Methods and apparatuses for analyzing proteins and other biological materials and xenobiotics within a sample. A specimen is generated, which may include an energy absorbent matrix. The specimen is struck with laser beams such that the specimen releases proteins. The atomic mass of the released proteins over a range of atomic masses is measured. An atomic mass window of interest within the range of atomic masses is analyzed to determine the spatial arrangement of specific proteins within the sample, and those specific proteins are identified as a function of the spatial arrangement. By analyzing the proteins, one may monitor and classify disease within a sample.

1 Claim, 9 Drawing Sheets

(56) References Cited

OTHER PUBLICATIONS

Brunelle et al. "Recent Advances in Biological Tissue Imaging with Time-of-Flight Secondary Ion Mass Spectrometry: Polyatomic Ion Sources, Sample Preparation, and Applications", Current Pharmaceutical Design, 2007, v. 13, pp. 3335-3343.*
IUPAC Compendium of Chemical Terminology 2nd Edition (1997).*
Clark, The Mass Spectra of Elements, 2000, http://www.chemguide.co.uk/analysis/masspec/elements.html.*
Rubakhin et al. "Imaging mass spectrometry: fundamentals and applications to drug discovery", DDT, c. 10, No. 12, pp. 823-837.*
Caprioli et al., "Molecular imaging of biological samples: Localization of peptides and proteins using MALDI-TOF MS," *Anal. Chem.*, 69:4751-4760, 1997.
Chaurand et al., "Direct profiling of proteins in biological tissue sections by MALDI mass spectrometry," *Anal. Chem.*, 71:5263-5270, 1999.
Cheng et al., "Predicting cancer progression in patients with stage T1 bladder carcinoma," *J. Clin. Oncol.*, 17:3182-3187, 1999.
Chicz et al., "Self-peptides bound to the type I diabetes associated class II MHC molecules HLA-DQ1 and HLA-DQ8," *International Immunology*, 6(11):1639-1649, 1994.
Chong et al., "Rapid screening of protein profiles of human breast cancer cell lines using non-porous reverse-phase high performance liquid chromatography separation with matrix-assisted laser desorption/ionization time-of-flight mass spectral analysis," *Rapid Commun. Mass Spectrom.*, 13:1808-1812, 1999.
Firlik et al., "Use of cytological preparations for the intra-operative diagnosis of stereotactically obtained brain biopsies: A 19-year experience and survey of neuropathologists," *J. Neurosurg.*, 91:454-458, 1999.
Hall, "Differential expression of thymosin genes in human tumors and in the developing human kidney," *Int. J. Cancer*, 48:672-677, 1991.
Iguchi, et al., "Decreased thymosin $\beta$.4 in apoptosis induced by a variety of antitumor drugs," *Biochem. Pharmacol.*, 57:1105-1111, 1999.
Jimenez, et al., "Direct mass spectrometric peptide profiling and sequencing of single neurons reveals differential peptide patterns in a small neuronal network," *Biochemistry*, 37:2070-2076, 1998.
Karas et al., "Matrix-assisted ultraviolet-laser desorption of nonvolatile compounds," *Int. J. Mass Spectrom. Ion Process.*, 78:53-68, 1987.
Klem et al., "Stereotatic breast biopsy in a community hospital setting", *Am.Surg.*, 65(8):737-740-1, 1999.
Levisetti, et al., "Imaging-SIMS (secondary-ion mass-spectroscopy) studies of advanced materials," *Scanning Microsc.*, 7:1161-1172, 1993.
Li, et al., "Direct peptide profiling by mass spectrometry of single identified neurons reveals complex neuropeptide-processing pattern," *J. Biol. Chem.*, 269:30288-30292, 1994.
Longacre and Hendrickson, "Diffusely infiltrative endometrial adenocarcinoma—an adenoma malignum pattern of myoinvasion," *Am. J. Surg. Pathol.*, 23:69-78, 1999.
Moroz et al., "Single-cell analyses of nitrergic neurons in simple nervous systems," *J. Exp. Biol.*, 202:333-341, 1999.
Pacholski and Winograd, "Imaging with mass spectrometry," *Chem. Rev.*, 99:2977-3005, 1999.
Paciucoi, et al., "Isolation of plasminogen activator, cathepsin H, and non-specific cross-reacting antigen from SK-PC-1 pancreas cancer cells using subtractive hybridization," *FEBS Lett.*, 385:72-76, 1996.
Richter et al., "Protocol for ultrarapid immunostaining of frozen sections," *J. Clin. Pathol.*, 52:461-463, 1999.
Shah et al., "Squash preparation and frozen section in intra-operative diagnosis of central nervous system tumors," *Acta Cytologica*, 42:1149-1154, 1998.
Silbergeld and Chicoine, "Isolation and characterization of human malignant glioma cells from histologically normal brain," *J. Neurosurg.*, 86:525-531, 1997.

Stoeckli et al., "Automated mass spectrometry imaging with a matrix-assisted laser desorption ionization time-of-flight instrument," *J. Am. Soc. Mass Spectrom.*, 10:67-71, 1999.
Stoeckli et al., "Imaging mass spectrometry: a new technology for the analysis of protein expression in mammalian tissues," *Nature Medicine*, 7(4):493-496, 2001.
Sun et al., "Actin monomer binding proteins," *Curr. Opin. Cell Biol.*, 7:102-110, 1995.
Thebauit et al., "Two-dimensional electrophresis and mass spectrometry identification of proteins bound by a murine monoclonal anti-cardiolipin antibody: A powerful technique to characterize the cross-reactivity of a single autoantibody," *Electrophoresis*, 21:2531-2539, 2000.
Todd et al., "Organic SIMS of biological tissue," *Anal. Chem.*, 69,:529A-535A, 1997.
Turner et al., "Intra-operative examination of the sentinel lymph node for breast carcinoma staging," *Am. J. Clin. Pathol.*, 112:627-634, 1999.
Valaskovic and Morrison, "Quantitative imaging ion microscopy—a short review," *Scanning Microscopy*, 6:305-318, 1992,.
Vlahou et al., "Development of a novel proteomic approach for the detection of transitional cell carcinoma of the bladder in urine," *American Journal of Pathology.*, 158:1491-1502, 2001.
Wang et al., "Quantitative laser scanning confocal autofluorescence microscopy of normal, premalignant, and malignant colonic tissues," *IEEE Trans. Biomed. Eng.*, 46:1246-1252, 1999.
Zhang and Caprioli, "Capillary electrophoresis combined with matrix-assisted laser desorption/ionization mass spectrometry; continuous sample deposition on a matrix-precoated membrane target," *Journal of Mass Spectrometry*, 31:1039-1046, 1996.
PCT Third Party Submission, issued in International Application No. JP/2003-536711, dated Apr. 15, 2004.
Todd et al., "Organic ion imaging of biological tissue with secondary ion mass spectrometry and matrix-assisted laser desorption/ionization," *Journal of Mass Spectrometry*, 36:355-369, 2001.
Grant Material Concerning: Caprioloi, "Spatial Analysis of Molecules in Tissue by Maldi-MS," Grant Proposal for the National Institutes of Health, Department of Health & Human Services, Grant Award Issue Date: Aug. 31, 1998.
Anderson and Anderson, "The human plasma proteome," *Molecular & Cellular Proteomics*, 1:845-867, 2002.
Arnaud, "Mass spec tackles proteins: Mass spectrometry shines in applications from proteomics to structural biology, but challenges remain," *Chemical & Engineering News*, 84(40):17-25, 2006.
Baggerly et al., "Reproducibility of SELDI-TOF protein patterns in serum: comparing datasets from different experiments," *Bioinformatics*, 20(5):777-785, 2004.
Good et al., "Neuromelanin-containing neurons of the substantia nigra accumulate iron and aluminum in Parkinson's disease: a LAMMA study," *Brain Research*, 593:343-346, 1992.
Kaddis and Loo, "Native protein MS and ion mobility: large flying proteins with ESI," *Anal. Chem.*, 79(5):1778-1784, 2007.
Kaddis et al., "Sizing large proteins and protein complexes by electrospray ionization mass spectrometry and ion mobility," *J Am Soc Mass Spectrom*, 18:1206-1216, 2007.
Larras-Regard and Mony, "Scanning ion images; analysis of pharmaceutical drugs at organelle levels," *International Journal of Mass Spectrometry and Ion Processes*, 143:147-160, 1995.
Levi-Setti et al., "Selective intracellular beryllium localization in rat tissue by mass-resolved ion microprobe imaging," *Biology of the Cell*, 63:77-82, 1988.
Linton and Bryan, "Comparison of laser and ion microprobe detection sensitivity for lead in biological microanalysis," *Anal. Chem.*, 57:440-443, 1985.
Morrison and Slodzian, "Ion microscopy," *Analytical Chemistry*, 47(11):932-943, 1975.
Myung et al., "Coupling desorption electrospray ionization with ion mobility/mass spectrometry for analysis of protein structure: evidence for desorption of folded and denatured states," *J. Phys. Chem. B.*, 110(145045-5051, 2006.
Myung et al., "Development of high-sensitivity ion trap ion mobility spectrometry time-of-flight techniques: a high-throughput nano-LC-

(56) References Cited

OTHER PUBLICATIONS

IMS-TOF separation of peptides arising from a *Drosophila* protein extract," *Analytical Chemistry*, 75(19):5137-5145, 2003.
Ruotolo et al., "Ion mobility-mass spectrometry analysis of large protein complexes," *Nature Protocols*, 3(7):1139-1152, 2008.
Ruotolo et al., "Ion mobility-mass spectrometry reveals long-lived, unfolded intermediates in the dissociation of protein complexes," *Angew. Chem. Int. Ed.*, 46:8001-8004, 2007.
Scarff et al., "Travelling wave ion mobility mass spectrometry studies of protein structure: biological significance and comparison with X-ray crystallography and nuclear magnetic resonance spectroscopy measurements," *Rapid Communications in Mass Spectrometry*, 22:3297-3304, 2008.
Seeley and Caprioli, "Molecular imaging of proteins in tissues by mass spectrometry," *Proc Natl Acad Sci USA*, 105(47):18126-18131, 2008.
Smith and Caprioli, "Following enzyme catalysis in real-time inside a fast atom bombardment mass spectrometer," *Biomedical Mass Spectrometry*, 10(2):98-102, 1983.
Smith et al., "Ion microscopy imaging of $^{10}$B from *p*-boronophenylalanine in a brain tumor model for boron neutron capture therapy," *Cancer Research*, 56:4302-4306, 1996.
Smith et al., "Monitoring copopulated conformational states during protein folding events using electrospray ionization-ion mobility spectrometry-mass spectrometry," *J Am Soc Mass Spectrom*, 18:2180-2190, 2007.
Srebalus Barnes and Clemmer, "Assessment of purity and screening of peptide libraries by nested ion mobility-TOFMS: identification of RNase s-protein binders," *Anal. Chem.*, 73:424-433, 2001.
Stone et al., "Surface-induced dissociation on a MALDI-ion mobility-orthogonal time-of-flight mass spectrometer: sequencing peptides from an 'in-solution' protein digest," *Anal. Chem.*, 73(10):2233-2238, 2001.

\* cited by examiner

METHODS AND APPARATUSES FOR ANALYZING BIOLOGICAL SAMPLES BY MASS SPECTROMETRY

This is a continuation of U.S. patent application Ser. No. 10/178,067, filed Jun. 21, 2002, now U.S. Pat. No. 6,756,586, which claims priority to U.S. Provisional Patent Application Ser. No. 60/329,719, filed Oct. 15, 2001. The entire contents of each of the foregoing applications is incorporated by reference.

Aspects of this invention were made with government support of the National Institute of Health, grant number GM58008. Accordingly, the government may have certain rights in this invention.

BACKGROUND OF THE INVENTION

1. Field of the Invention

The present invention relates generally to the fields of medical imaging, analysis, monitoring and diagnostics. More particularly, it provides apparatuses and methods for analyzing proteins in samples. Even more particularly, it may be used in the direct profiling of diseased tissue by mass spectrometry; this, in turn, may be used for the assessment of disease classification, development and treatment.

2. Description of Related Art

Every year about 1.5 million Americans are diagnosed with cancer. Tragically about 500,000 people die of the disease every year. Cancer can affect people in a variety of different ways: about 11% of cancer patients are diagnosed with colorectal cancer, 15% with prostate cancer, 20% with lung cancer, 15% with breast cancer, and 2% with brain cancer. The ability to effectively identify specific tumor markers in proliferating areas of the tumors would therefore be a beneficial step in diagnosing, monitoring, analyzing, and treating such tumors and, in general, a wide variety of other ailments.

Matrix-assisted laser desorption ionization mass spectrometry (MALDI MS) is an analytical technique having high sensitivity, ease of use, and compatibility as an effective off-line method for different types of sample analysis. Static sampling systems using MALDI MS have demonstrated extremely high sensitivities, as illustrated by attomole sensitivity for the analysis of peptides contained in complex physiological salt solutions. Further, matrix precoated cellulose targets have been used to analyze 100% aqueous samples without the need of further treatment with organic solvents.

Several reports have described the use of MALDI for the analysis of specific peptides in whole cells. Several papers describe the analysis of some neuropeptides directly in single neurons of the mollusk *Lymnaea stagnalis*. Isolated neurons were ruptured, mixed with small volumes of matrix, and analyzed. The ability of MALDI MS to be used to elucidate some of the metabolic processing involved in neuropeptide production from precursor peptides has also been demonstrated. Also, a single neuron from *Aplypsia californica* was analyzed for several specific neuropeptides using a procedure involving removal of excess salt by rinsing with matrix solution.

A considerable amount of work has been described for use of secondary ion mass spectrometry (SIMS) for the spatial arrangement of elements in surfaces of samples including biological tissue and organic polymers. In addition, there have been recent efforts to apply the SIMS technique to organic compounds and metabolites in biological samples. At least one report describes conditions for generating secondary ion mass spectra from samples with choline chloride and acetylcholine chloride deposited onto specimens of porcine brain tissue. Samples were then exposed to a primary ion beam of massive glycerol clusters. Images generated from the spacially arranged SIMS spectra were obtained that reflected the identity and location of the spiked analytes.

U.S. Pat. No. 5,808,300 which is incorporated herein by reference, describes a method and apparatus for imaging biological samples with MALDI MS. Its techniques can be used to generate images of samples in one or more m/z pictures, providing the capability for mapping the concentrations of specific molecules in X,Y coordinates of the original biological sample. Analysis of a biological sample can be carried out directly or to an imprint of the sample. The image attained in the analysis can be displayed in individual m/z values as a selected ion image, as summed ion images, or as a total ion image. The imaging process may also be applied to other separation techniques where a physical track or other X, Y deposition process is utilized.

U.S. Pat. No. 5,272,338 which is incorporated herein by reference, describes a specific instrument setup using a liquid metal ion source to ionize a sample in a mass spectrometer, and then a laser beam to irradiate the ejected molecules and resonantly ionize them. The method involves a technique commonly referred to as SIMS/cross beam laser ionization.

U.S. Pat. Nos. 5,372,719 and 5,453,199 which are incorporated herein by reference, disclose techniques for preparing a chemically active surface so that when a sample is exposed to this surface, a chemical image of the sample is deposited on the surface. The disclosed methods involve the separation of molecules by sorbents.

U.S. Pat. No. 5,607,859 which is incorporated herein by reference, describes a method for the MS determination of highly polyionic analytes by the interaction of oppositely charged molecules.

U.S. Pat. No. 5,569,915 which is incorporated herein by reference, discloses an MS instrument for fragmenting molecules in the gas phase.

U.S. Pat. No. 5,241,569 which is incorporated herein by reference, describes neutron activation analysis for detecting gamma rays and beta-electrons from radioactively labeled samples. This technique may be used to locate elements in a sample.

Although techniques referenced above show at least a degree of utility in performing certain types of general analysis, shortcomings remain. For instance, current techniques used for rapid decisions in the clinical laboratory often involve the analysis of frozen sections using light microscopy. Such techniques, however, are, at times, non-specific and inaccurate. More importantly, conventional technology does not involve techniques that effectively employ the capability of MALDI MS to analyze and effectively depict a quantity of molecules of interest with a specific molecular mass or within a selected molecular mass window or as a function of their position on the test sample. Further, conventional technology does not employ MALDI MS techniques to effectively analyze proteins in clinical samples. Still further, conventional technology does not use MALDI MS techniques to perform direct profiling of diseased tissue, which in turn may be used for the assessment of disease classification, development and treatment.

SUMMARY OF THE INVENTION

The molecular analysis and imaging of proteins and other biological materials in tissues is an important part of medical imaging, monitoring, analysis, diagnostics, disease classification, and treatment of a variety of disorders. As used herein "biological material" is to be interpreted broadly and can include, for example, nucleic acids, lipids, carbohydrates or any molecule covered in Biochemistry (Stryer, et al., 2002). Specifically, molecular analysis and imaging may be used as an integral building block in strategies designed to locate specific proteins that are more highly expressed in tumors relative to normal tissue. Likewise, it may be used to locate specific proteins diminished in expression relative to normal tissue. One of the many aims of the techniques of this disclosure is the molecular analysis and imaging of peptides and proteins in brain tumors, specifically in human glioblastoma.

Generally speaking, this disclosure involves mass spectrometric techniques of matrix-assisted laser desorption ionization mass spectrometry (MALDI MS) and electrospray ionization mass spectrometry (ESI MS) to image and detect proteins and other biological materials in tissue. Certain aspects of this disclosure employ the molecular specificity and sensitivity of mass spectrometry (MS) for the direct mapping and imaging of biomolecules present in tissue sections. This technology has been developed using MALDI MS and may be used for the analysis of peptides and proteins present on or near the surface of samples, such as tissue sections. Imaging MS brings a new tool to bear on the problem of unraveling and understanding the molecular complexities of cells. It joins techniques such as immunochemistry and fluorescence microscopy for the study of the spatial arrangement of molecules within biological tissues.

In one respect, the invention is a method of analyzing proteins within a sample. A specimen including an energy absorbent matrix is generated. The specimen is struck with a laser beam such that a predetermined first laser spot on the specimen releases first sample proteins. The molecular mass of the released first sample proteins is measured over a range of molecular masses. The specimen is moved relative to the laser beam a predetermined linear distance functionally related to a size of the predetermined first laser spot. The specimen is struck again with the laser beam such that a predetermined second laser spot on the specimen releases second sample proteins. The molecular mass of the released second sample proteins is measured over a range of molecular masses. An molecular mass window of interest within the range of molecular masses is analyzed to determine the specific proteins within the sample. The determined specific proteins can be mapped as a function of the spatial arrangement.

In other respects, the specimen may include tumor-bearing tissue. The tumor-bearing tissue may include brain tissue. It may include prostate tissue. It may include colon tissue. The step of generating specimen may include generating a fresh, or frozen section. It may also include generating individual cells or clusters isolated by laser-capture microdissection or other cell isolation techniques. As used herein "separate layers" refers to separate two dimensional sections of a tumor. The step of analyzing the molecular mass window of interest may include graphically depicting the mass of proteins within the molecular mass window of interest as a function of the linear distance between the first spot and the second spot. The specimen may be dried prior to being struck with laser beams. Proteins within the atomic window of interest from the first laser spot may be analyzed while the laser beam strikes the second laser spot. The linear distance of movement between successive laser spots may be less than twice the width of each of the successive laser spots. The step of identifying the specific proteins may involve extraction, HPLC fractionation, proteolysis, mass spectrometric sequencing of one or more fragments and protein database searching.

In another respect, the invention is a method for classifying disease. A diseased specimen including an energy absorbent matrix is generated. The specimen is struck with a laser beam such that a predetermined first laser spot on the specimen releases first sample proteins. The molecular mass of the released first sample proteins is measured over a range of molecular masses. The specimen is moved relative to the laser beam a predetermined linear distance functionally related to a size of the predetermined first laser spot. The specimen is again struck with the laser beam such that a predetermined second laser spot on the specimen releases second sample proteins. The molecular mass of the released second sample proteins is measured over a range of molecular masses. An molecular mass window of interest within the range of molecular masses is analyzed to determine the spatial arrangement of specific proteins within the sample. The specific proteins are identified as a function of the spatial arrangement, and the identified specific proteins are correlated with one or more diseases to classify the diseased specimen.

In another respect, the invention is a method for monitoring the development of a specimen over time. A specimen including an energy absorbent matrix is generated at a first time. The specimen is struck with a laser beam such that a predetermined first laser spot on the specimen releases first sample proteins. The atomic mass of the released first sample proteins is measured over a range of atomic masses. The specimen is moved relative to the laser beam a predetermined linear distance functionally related to a size of the predetermined first laser spot. The specimen is again struck with the laser beam such that a predetermined second laser spot on the specimen releases second sample proteins. The atomic mass of the released second sample proteins is measured over a range of atomic masses. An atomic mass window of interest within the range of atomic masses is analyzed to determine the spatial arrangement of specific proteins within the sample. The specific proteins are identified as a function of the spatial arrangement. These steps are repeated, and the specific proteins identified at the first time are compared with the specific proteins identified at the second and subsequent times to monitor the development of the sample or, more particularly, disease of the sample.

In other respects, the method may also include correlating the identified specific proteins and other biological materials at the first or second times with one or more diseases. The method may also include treating those one or more diseases.

In another respect, the invention is an apparatus for analyzing a sample containing proteins. The apparatus includes a laser source, a moving mechanism, a mass analyzer, a computer, a display, and means for correlating molecular mass. The laser source is adapted for sequentially striking a specimen with a laser beam at a plurality of laser spots on the specimen for sequentially releasing sample proteins from each laser spot. The moving mechanism is adapted for sequentially moving the specimen relative to the laser beam a predetermined linear distance functionally related to the size of the laser spots prior and subsequent to the movement. The mass analyzer is adapted for measuring the molecular mass of the released sample proteins over a range of molecular masses. The computer is adapted for receiving molecular mass data from the mass analyzer. The display is adapted for depicting molecular mass within an molecular mass window of interest as a function of individual laser spots on the specimen. The means for correlating atomic molecular mass includes means for performing such a correlation so that molecular masses may be correlated with one or more specific proteins. The means for performing this function are described herein and in the incorporated references and may include a wide variety of mechanisms including databases or any other computerized methodology and software for implementing the correlation steps discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 2A shows an optical image of a frozen section mounted on a gold-coated plate. FIG. 2B shows m/z 8,258 in the regions of the cerebral cortex and the hippocampus. FIG. 2C shows m/z 6,716 in the regions of the substantia nigra and medial geniculate nucleus. FIG. 2D shows m/z 2,564 in the midbrain.

FIG. 3A shows a human glioblastoma slice mounted on a metal plate, coated with matrix (the lines are from ablation of matrix with the laser). FIGS. 3B-3D show mass spectrometric images of proteins showing high concentration in the proliferating area of the tumor (FIG. 3D) and other proteins present specifically in the ischemic and necrotic areas (FIGS. 3B and 3C).

DESCRIPTION OF ILLUSTRATIVE EMBODIMENTS

Techniques of this disclosure overcome deficiencies in the art by providing ways to effectively analyze proteins in samples. These techniques have vast applications in the imaging, monitoring, diagnosis, and treatment of a myriad of disorders. In some embodiments, specific tumor markers may be analyzed, imaged, identified, and monitored for diagnostic and/or treatment regimes.

Figure 7:
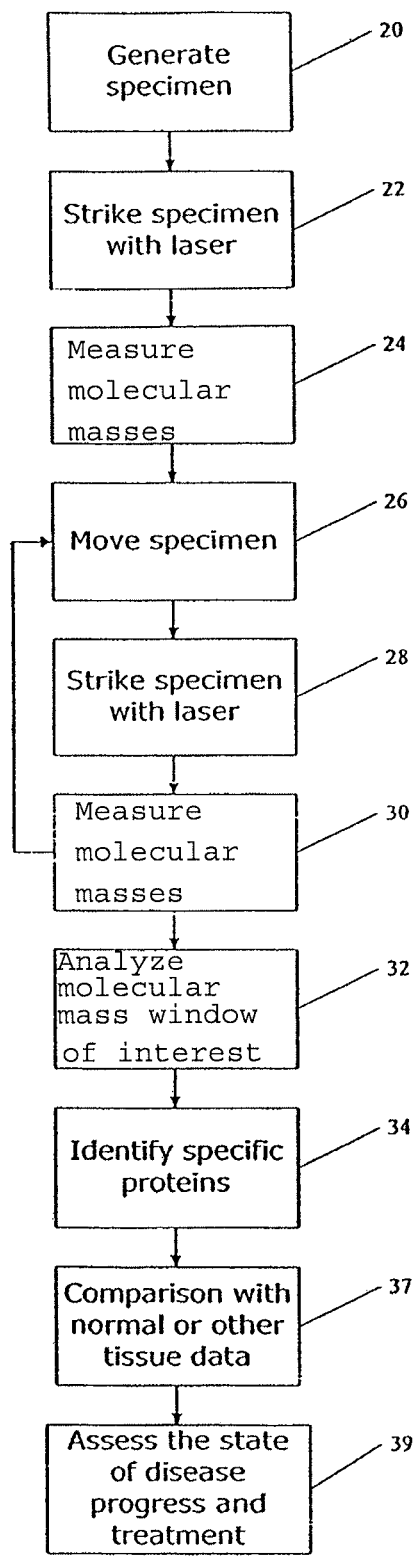
FIG. 7 is a flow chart illustrating method steps according to embodiments of the present disclosure.

FIG. 7 illustrates certain exemplary methodology of the present disclosure. In step 20, a sample is generated. As discussed below, this sample may or may not include an energy absorbent matrix. In one embodiment, the specimen may be a fresh, frozen section that may be profiled directly. Such a specimen may obviate the need for cumbersome sample preparation steps required by some conventional methodology referenced in the art. The specimen may also be individual cells or clusters, which may be isolated by laser-capture microdissection. The specimen may include tissue such as, but not limited to, brain tissue, prostate tissue, or colon tissue. It may be animal or human tissue, and it may be tumor-bearing tissue. If the specimen is a tumor-bearing tissue, the techniques described herein may be used in intraoperative assessment of the surgical margins of tumors. In one embodiment, the specimen may include cancerous tissue. Some examples of cancer tissues that may be analyzed include, but are not limited to, testicular, prostate, lung, breast, colon, and brain cancer. In other embodiments, the tissue may be normal. Tissue specimens may be obtained by any means known in the art, including surgical means. If a tissue is obtained surgically, it is advantageous that the tissue be intact and the location of the tissue be known prior to removal. Tissue may be obtained from tissue grown in any medium, and the tissue obtained may be stored for later analysis for an indefinite period of time according to methods known in the art. With the benefit of this disclosure, those having skill in the art will recognize that other types of specimens and tissue may be analyzed using the very techniques described herein, without insubstantial modifications.

The sample may include an energy absorbent matrix, which is a material that will absorb UV or energy at other wavelengths. This matrix may include an organic or inorganic compound having a relatively high extinction coefficient for absorption of energy and may be applied in a thin layer over the sample or otherwise be incorporated in the sample. Example energy absorbent matrixes include but are not limited to 2,5-dihdroxybenzoic acid and $\alpha$-cyano-4-hydroxycinnamic acid. The energy absorbent matrix may be applied using electrospray, pneumatic spray, spin coating, dip coating or any other appropriate method.

The sample may include a tissue without an additional energy absorbent matrix. Here, the energy is absorbed only by the sample and is not first incident on an exogenous energy absorbing matrix. Sample preparation is simpler in that the additional step of applying the matrix is not required.

In step 22, the specimen is struck with a laser. Prior to this step, the specimen may be dried. The laser referenced in step 22 is configured so that it strikes a predetermined first spot on the specimen, which releases proteins from the specimen. The size and position of the laser spot may be varied as is known in the art. The type of laser and its power settings may likewise be adjusted as is known in the art.

In step 24, the molecular mass of released proteins are measured over a range of molecular masses. This step may be accomplished according to general spectroscopy knowledge and instrumentation known in the art.

In step 26, the specimen is moved relative to the laser beam. This translation may be by a predetermined distance. This distance may be functionally related to the size of the laser spot to achieve an effective scan pattern. By varying the amount of the translation, one may affect the resolution of the scan, as is known in the art. The mechanism used to translate the specimen may be any one of a number of translation stages available commercially. The type of translation may be one, two, or three dimensional, depending on the application. In one embodiment, the distance of movement between successive laser spots may be less than twice the width of each of the successive laser spots.

In steps 28 and 30, additional data is taken after the specimen has been moved. This data-gathering is described above in relation to steps 22 and 24. As illustrated, steps 26-30 may be repeated as desired to set up an effective scan of the specimen. In one embodiment, the scan may involve moving the sample and obtaining data several times in order to generate an X,Y two dimensional pattern. Successive sample sections can be analyzed to give a 3-D data set. As will be understood by those having skill in the art, data analysis steps such as steps 30, 32, and 34 may be undertaken while additional scans are being made. In other words, data processing may take place at the same time as the specimen is being scanned.

In step 32, a window of interest is defined from among the range of masses encompassed by the released proteins (the proteins released from the specimen due to the laser beam). This window of interest may include the entire range of masses of the released proteins or any portion thereof. Within the window of interest, masses of the released proteins may be analyzed so that the spatial arrangement of the released proteins may be determined. In other words, the location of released proteins may be correlated to their position (e.g., to the location of one or more laser spots) by reference to their measured mass within the window of interest. In one embodiment, this step may involve graphically depicting the mass of proteins within the molecular mass window of interest as a function of the linear distance between a first laser spot and a second laser second spot (and/or subsequent laser spots). Those having skill in the art will recognize that other mapping techniques known in the art may be applied to this data analysis step.

In step 34, the proteins analyzed in step 32 may be identified by reference to, for example, its mass number or other distinguishing characteristics. This particular step may utilize one or more of techniques known in the art. In one embodiment, step 34 may be facilitated by extraction, HPLC fractionation, proteolysis, mass spectrometric sequencing of one or more fragments and protein database searching.

In step 37, comparison may be made with data representing a normal tissue or sample, and/or comparison may be made with other types of data. For instance, comparison may be made with normal tissue or data associated with a normal tissue. In this manner, one may assess, for example, the state of disease progress and treatment, as shown in step 39.

Figure 8:
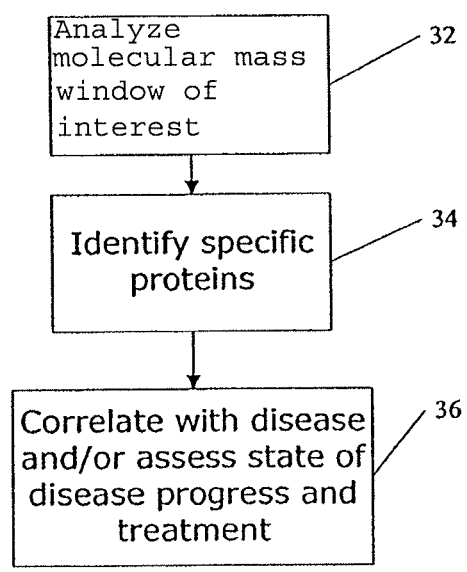
FIG. 8 is a further flow chart illustrating method steps according to embodiments of the present disclosure.

With the framework of FIG. 7 in place, one may engage in a number of useful medical activities including but not limited to the diagnosis, monitoring, and treatment of disease. As shown in FIG. 8, once specific proteins are identified, one may then correlate those proteins with one or more diseases to classify (or identify) diseases within the specimen. For instance, if marker proteins are identified (step 34) those proteins may be associated with their corresponding disease. The proteins may also be assessed to determine the state of the disease progress and treatment, such as in step 36, which is similar to steps 37 and 39 of FIG. 7. One or more markers may signal one or more diseases, as is known in the art. Disease and the general state of a specimen or patient may be monitored, in turn, by identifying specific proteins and/or diseases over an extended period of time. For instance, one may perform steps of FIG. 7 at a first time and at a later, second time. By comparing the results of the analyses, one may track the progression and location of disease. For example, at a second time, the presence of a specific marker may have decreased in a certain area, which may indicate that a corresponding disease is being effectively treated. The period of time between the first and second data analyses may be varied according to need, as will be understood by those having skill in the art. In this vein, one embodiment of this disclosure involves using the techniques of FIG. 7 to monitor and perhaps restructure chemotherapy treatment. The current state of a patient's tissues may be monitored over time, and one may assess the effectiveness of a treatment regimen over the course of treatment, thereby allowing doctors to adjust that regimen to optimize for beneficial results.

Figure 9:
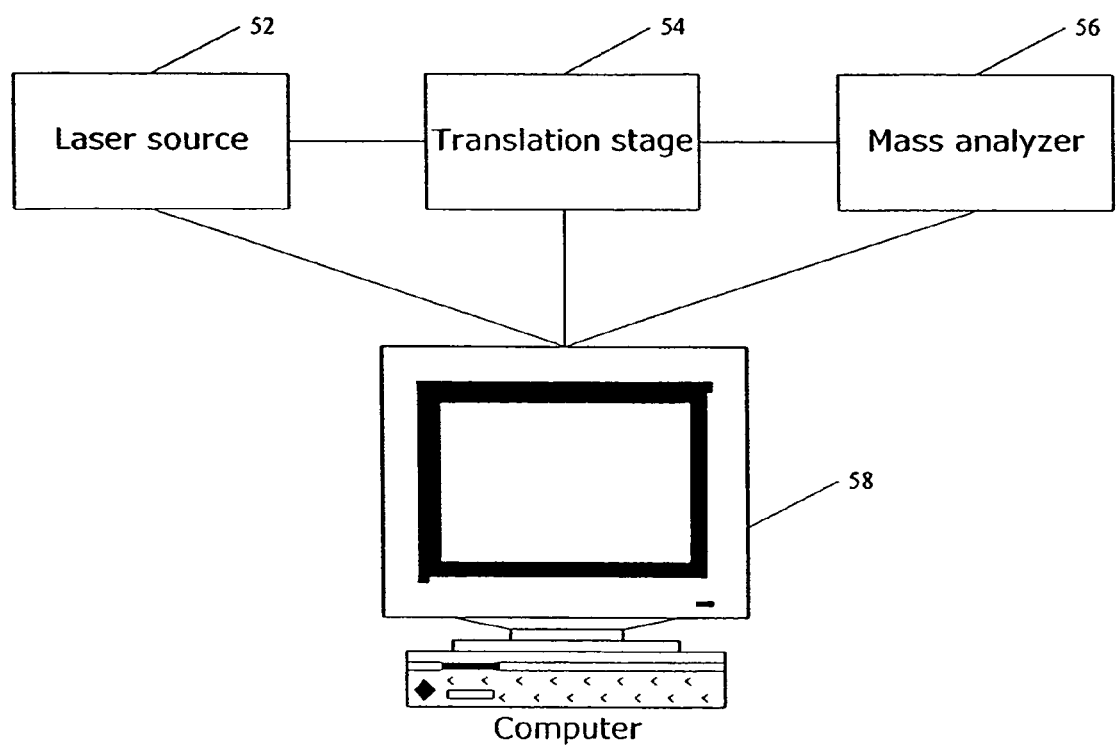
FIG. 9 is a schematic diagram of an apparatus suitable to perform steps in accordance with embodiments of the present disclosure.

FIG. 9 shows an apparatus for practicing the steps depicted in FIGS. 7-8 and described above. As illustrated, the apparatus includes a laser source 52, a translation stage 54, a mass analyzer 56, and a computer 58. The laser source 52 is configured to sequentially and controllable strike a specimen at a plurality of laser spots for sequentially releasing proteins from the specimen. The translation stage 54 may generally be any moving mechanism for moving the specimen. It moves the specimen relative to the laser beam a predetermined distance. This distance may be functionally related to the size of the laser spots to control resolution. The mass analyzer 56 measures molecular mass of released proteins from the specimen over a range of molecular masses. Computer 58 receives molecular mass data from mass analyzer 56 and may include a display for depicting molecular mass within an molecular mass window of interest as a function of individual laser spots on the specimen. The display for depicting molecular mass may alternatively be separate from computer 56. In one embodiment, computer 56 may also be used to correlate the molecular mass within the molecular mass window with one or more specific proteins using software known in the art. Alternatively, another computer, a database, a network, or manual methods may be used for achieving this correlation.

The techniques described herein may be used to monitor and classify cancer and other diseases. This includes the diagnosis and prognosis of cancers as well as analysis of cancer treatment procedures. The cancer evaluated may include, but is not limited to, brain, prostate, colon, breast, lung, ovarian, pancreas, rectal and renal cancers.

In one embodiment, breast cancer can be monitored and classified by methods of the current invention. In current practice, breast biopsy can be assayed using the chip technology known as LORAD (Klem, D. et al., 1999). The biopsy sample analyzed using LORAD can also be analyzed in conjunction with the techniques disclosed herein, or separately.

As used herein, the term "proteins" is used broadly and is defined to include peptides and polypeptides.

The methods described herein may be used to analyze therapeutic agents as well as proteins. The method can also be used to monitor the development of the sample by correlating protein changes with respect to the therapeutic agent used during the course of therapy. Therapeutic agents may be studied in a specimen to monitor and classify disease and treatment. One or more therapeutic agents may include, but are not limited to, DNA, chemotherapeutic drugs, or anticancer drugs. The therapeutic agents can also be selected from any drug listed in the Physician's Desk Reference, (for example, the 2002 edition) or from any other source known in the art. The therapeutic agents may also be one or more drugs comprising of paclitaxel, campothecins, epothilones, docetaxel, etopside, doxorubicin, daunomycin, geldanamycin, cisplatin, carboplatin, methotrexate, cyclosporin, emodin, amphotericin B, etc. In one embodiment, agents may be selected from the group consisting of chemotherapeutics, antibiotics, antivirus, antiinflammatories, or radiosensitizers.

Metabolites of therapeutic agents may also be analyzed by use of the methods described herein. These metabolites may be found in for example tissue, blood, plasma or urine. As used herein, the term "metabolite" refers to a compound produced from chemical changes of a therapeutic agent or drug in the body. An example of a drug is morphine whose effect is primarily due to one of its glucuronide conjugate metabolites.

As used herein, the phrase "tumor-bearing tissue" refers to tissue that contains one or more cells that are either abnormal or diseased. As known in the art, with some tumors, such as breast, ovarian, or pancreas, not all cells within the affected tissue are necessarily abnormal. Thus, tumor-bearing tissue includes tissue where only some of the cells are abnormal.

In one embodiment, the specimen may comprise biological samples for testing that are not tissue based. For example, blood and urine samples may be used. Blood may be taken from the patient and prepared. Whole blood may be used, or the sample may include red blood cells, white blood cells, or plasma. The cells can be washed one or more times with a saline solution, and they may also be lysed before analysis. Urine samples may also be prepared before analysis. For non-tissue biological sample, the sample may be prepared with or without an energy absorbent matrix.

As used herein, the phrase "monitoring the development" of a specimen over time refers to monitoring the specimen for any changes in disease progression over time. This may include monitoring the advance or recession of a disease. It also may include monitoring a specimen with a high probability for a disease for the onset of disease, monitoring a specimen after diseased tissue has been removed to determine if the disease reappears, or monitoring a specimen from patients at risk prior to the appearance of disease.

As used herein, the term "electroblotting" refers to a technique known in the art for transferring proteins or other biological samples from gel to membrane. Contact blotting, a similar technique in which electric current is not used, may be used in place of electroblotting to transfer specimens. Similarly, capillary transfer may be used.

As used herein, the term "cell fractionation" refers to a broad set of techniques that either separate or isolate cells. These techniques usually occur in two stages, including homogenization (disrupting the tissue and releasing cellular components) and centrifugation (separating the individual components according to density, size and shape). Cell fractionation may be used to generate a specimen by isolating individual cells or cell clusters. Cellular fractionating can be done by methods known in the art such as flow cytometry. One suitable technique is cell sorting.

As used herein, the phrase "optical system" refers to one or more lens, or other optical components used generally to direct radiation, such as light from a laser. For example, an optical system may be used to focus and align a laser beam at a desired location, to achieve a particular diameter and power, and/or and obtain a preferred beam profile. A laser mask may also be used for selectively shaping or defining the size of laser spots on a test specimen. Such a mask may block parts of the laser beam not intended for use so that the beam profile is well defined in both shape and size when it is incident on the specimen.

As used in the specification, "a" or "an" may mean one or more. As used in the claims in conjunction with the word "comprising", the words "a" or "an" mean one or more.

EXAMPLES

The following examples are included to demonstrate specific, non-limiting embodiments of the disclosure. It should be appreciated by those of skill in the art that the techniques disclosed in the examples that follow represent techniques discovered by the inventor to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention. All such changes are to be included within the scope of this disclosure.

Example 1

General Methodology

Figure 1:
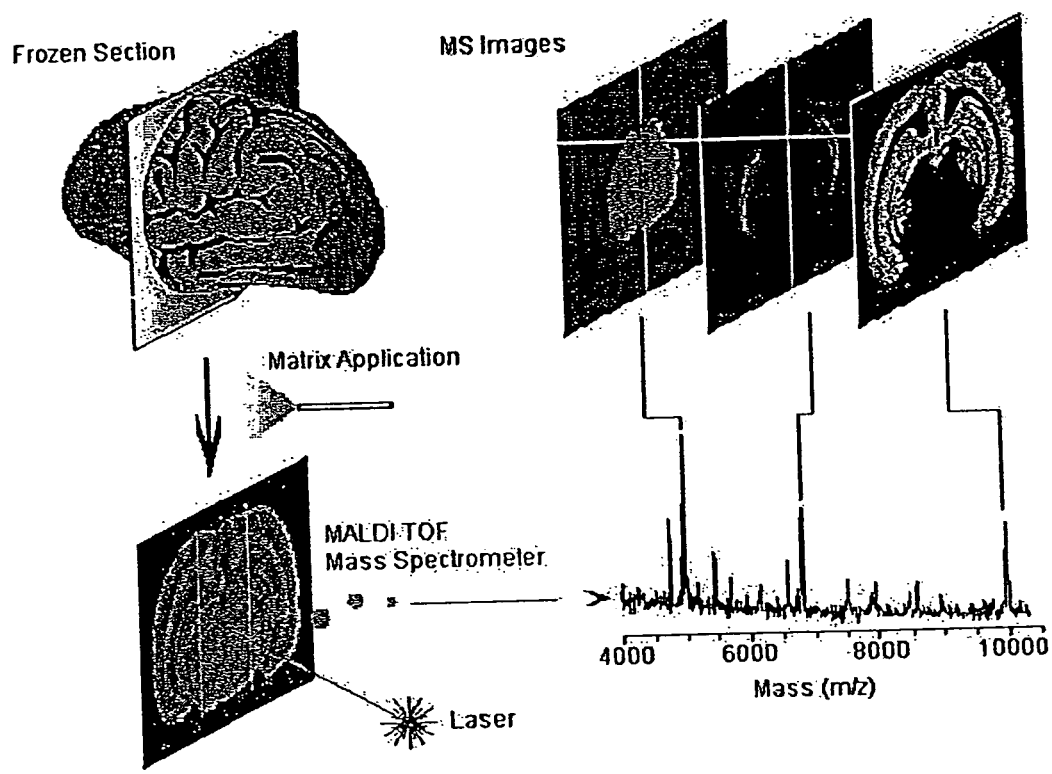
FIG. 1 is a schematic diagram of methodology for analyzing samples according to embodiments of the present disclosure.

FIG. 1 illustrates methodology suitable for embodiments of this disclosure. The illustrated methodology of FIG. 1 was designed for the spatial analysis of tissue by MALDI mass spectrometry. In this embodiment, frozen sections are mounted on a metal plate, coated with an UV-absorbing matrix and placed in a mass spectrometer. A pulsed UV laser desorbs and ionizes analytes from the tissue and their m/z values are determined using an instrument such as a time-of-flight analyzer. From a raster over the tissue and measurement of the peak intensities over several spots (which may be thousands of spots), mass spectrometric images may be generated at specific molecular weight values.

For the molecular image analysis, tissue samples can be prepared using several protocols: (a) direct analysis of fresh frozen sections, individual cells or clusters of cells isolated by laser-capture microdissection or other cell isolation procedure, or (b) contact blotting of a tissue on a membrane target. In a typical preparation procedure, the inventor and assistants mounted a frozen section of tissue on a stainless steel target plate, coated it with a solution of matrix (for example, sinapinic acid), then dried and introduced into a vacuum inlet of a mass spectrometer (a Voyager Elite DE, Applied Biosystems, Framingham, Mass. was used). The instrument was controlled by MS imaging software written in the inventor's laboratory, but any number of commercial software packages are equally well-suited to generate results discussed herein. The inventor and assistants created molecular images from a raster over the surface of the sample with consecutive laser spots (25 µm in diameter). The laser position was fixed and the sample plate was repositioned for consecutive spots. Each spot produced a mass spectrum obtained from molecules present within the irradiated area. Typically, each mass spectrum was the average of 50 laser shots acquired using a fast transient recorder PC board (DP211, Acqiris, Geneva, Switzerland). With a laser frequency of 20 Hz, the time cycle was about 2.5 seconds per data point, including acquisition, data download to the computer, data processing and repositioning of the sample stage. A typical data array was 1,000-30,000 spots depending on the desired image resolution, which contains the intensity of ions desorbed at each spot in a molecular weight range of 500 D to over 80 kD. For most tissue sections, over 200 protein and peptide peaks were recorded in the mass spectrum from each spot ablated by the laser. An MS image or molecular weight-specific map of the sample could be produced at any desired molecular weight value. It is commonly possible to generate individual maps to verify the presence, molecular weight and location of proteins. In the fullest extent, from a single raster of a piece of tissue, imaging MS could produce hundreds of image maps each at a discrete molecular weight value.

Example 2

Application to Mammalian Tissue

Figure 2:
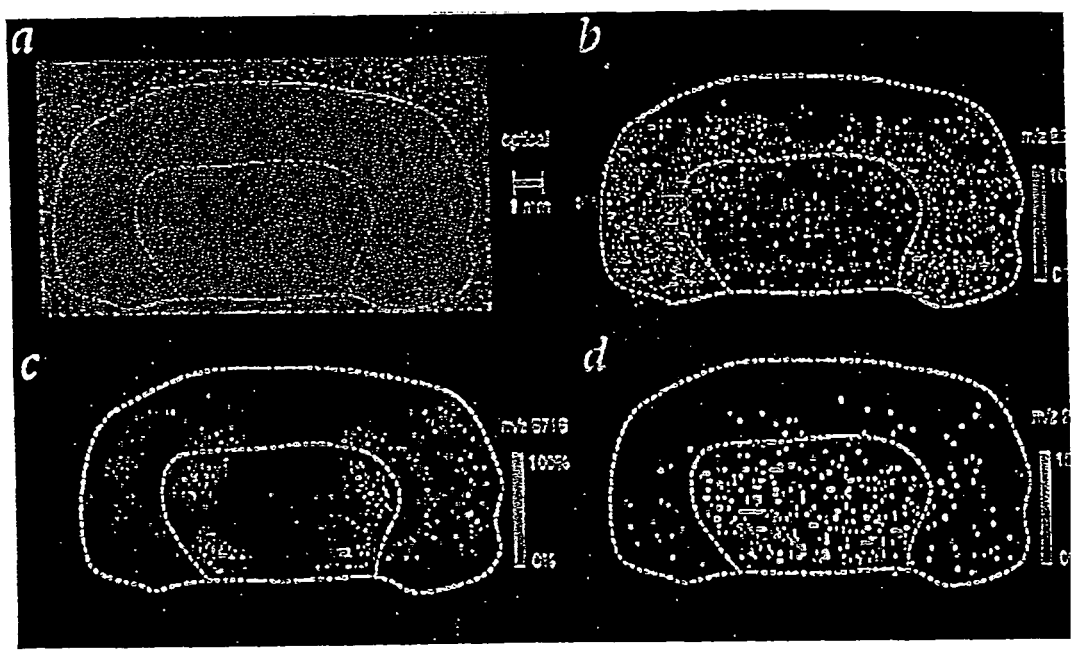
FIGS. 2A, 2B, 2C, and 2D show mass spectrometric images of a mouse brain section in accordance with embodiments of the present disclosure.

The inventor and assistants have used imaging MS to study normal tissue sections from mouse brain and human brain tumor xenograph sections. These samples contained well-defined regions, many of which had subsets of proteins and peptides in a unique distribution or array. The bilateral symmetry of the brain provided an internal confirmation of the localized distribution of proteins and the homogeneity of the prepared tissue sections. An optical image of the normal mouse brain section fixed on a metal plate and coated with matrix is shown in FIG. 2A. The inventor and assistants scanned the section by acquiring 170×90 spots with a spot-to-spot center distance of 100 µm in each direction. Ions occurring in 82 different mass ranges were recorded, and images were created by integrating the peak areas and plotting the relative values using a color scale. For specific molecular images, data was acquired in a window delimited by two mass-to-charge (m/z) units on either side of the molecular peak. Although many of the protein signals were common to all areas of the brain, some were found to be highly specific for a given brain region. For example, the protein detected at m/z 8258±1 (FIG. 2B) was present in the regions of the cerebral cortex and the hippocampus; the protein at m/z 6716±1 (FIG. 2C) was localized in the regions of the substantia nigra and medial geniculate nucleus; and the peptide at m/z 2564±1 was in the midbrain (FIG. 2D). These ions are [M+H]$^+$ species, and the molecular weights of the compounds were obtained by subtracting the weight of a proton, nominally 1 m/z unit from the measured m/z value. Identification of the proteins can be done through extraction, HPLC fractionation, proteolysis, mass spectrometric sequencing of one or more of the fragments and protein database searching.

Example 3

Preparation of Tumor-Bearing Tissue for Molecular Imaging

Tumor-bearing tissues were generated by subcutaneous implantation of human glioblastoma cells (D54) into the hind limb of a nude mouse. After tumors grew to about 1 cm in diameter, they were surgically removed them from the mouse and immediately frozen using liquid nitrogen. For image analysis, the inventor cut the tumor tissue using a microtome in 12-µm thick sections orthogonal to the point of attachment to normal tissue. Frozen sections were processed following the protocol described above before image analysis by MS.

Figure 3:
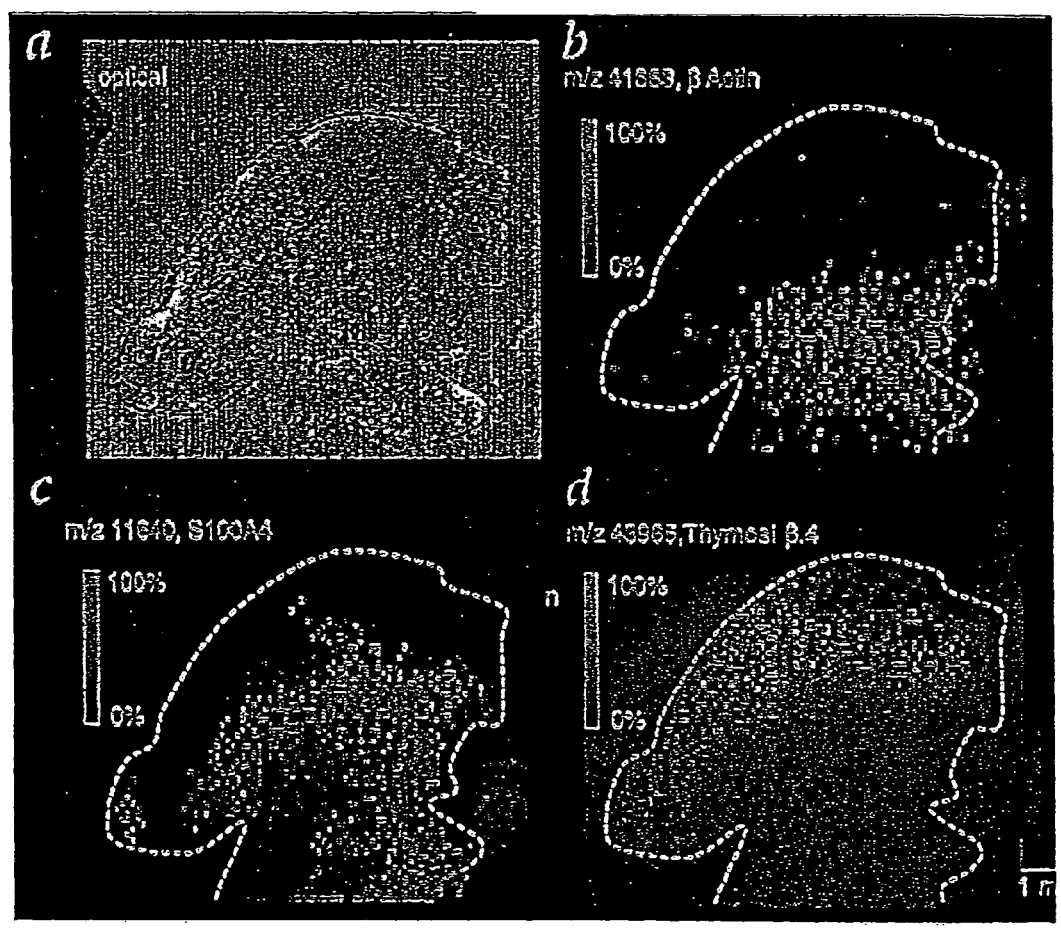
FIGS. 3A, 3B, 3C, and 3D show protein images in accordance with embodiments of the present disclosure. In particular, these figures show selected protein images from a glioblastoma section.

The optical image of a frozen human glioblastoma section taken immediately following mass spectrometric imaging is shown in FIG. 3A. The orientation in FIG. 3A is such that the actively growing area of the tumor is at the top of the figure, and the point where the tumor was attached to the healthy tissue at the bottom. The fine line (cross-hatched) pattern on the optical image was produced by laser ablation of the surface during the scan.

Example 4

Molecular Imaging of Tumor Sections

Figure 4:
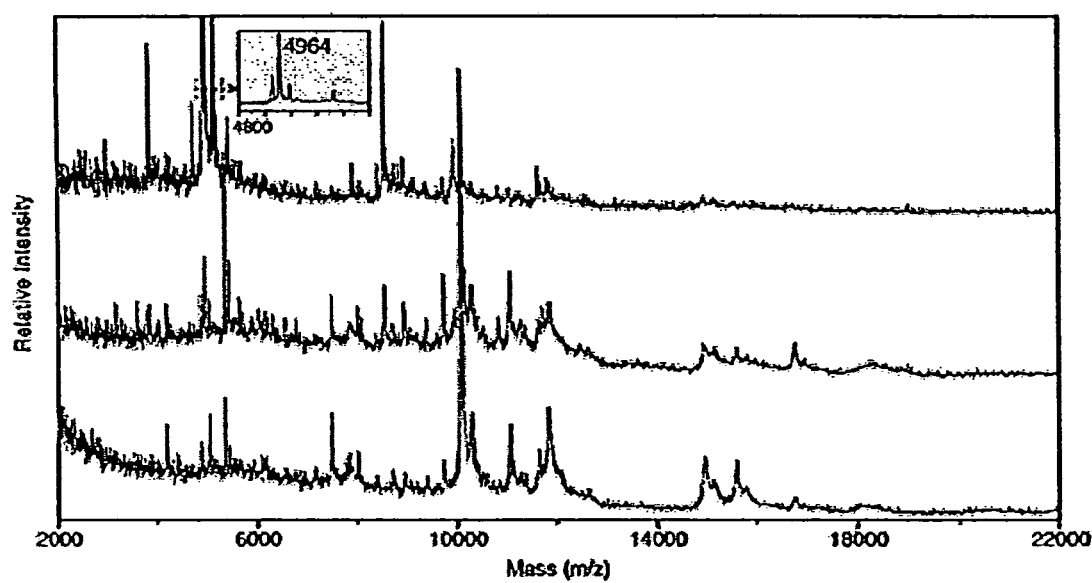
FIG. 4. shows MALDI mass spectra taken at different locations within a glioblastoma slice (FIG. 3). Over 150 different peaks could be detected, with some of them having a distinct spatial distribution in the tissue. The top line is the distal and most active area of tumor proliferation; the middle line is an ischemic area; the bottom line is a necrotic area of the tumor. The inset shows an expanded portion of the spectrum in the region of thymosin $\beta$.4.

Mass spectrometric images were produced from a raster over an area of 8.5 mm×8 mm (image spots 100 µm apart on center). During the scan, the inventor and assistants recorded images of ions in 45 mass ranges and the mass spectra were saved for further analysis. Three mass spectrometric images of molecules present in distinct areas of the tumor are shown in FIGS. 3B-3D. In this figure, black and white contrast is used to represent different ions, with black saturation a function of the relative intensity. Overall, over 150 different proteins were detected, with many being present in all parts of the tissue. Individual selected proteins were identified as described below. Three different mass spectra were taken from different regions of the glioblastoma during the scan (FIG. 4). These spectra show differences in protein expression in different parts of the tumor.

The proliferating area of the tumor was of particular interest with many proteins being expressed at higher levels relative to normal tissue. For example, the protein of molecular weight 4,964 (FIG. 3D) was localized only in the outer area of the tumor. Other proteins, such as that of molecular weight 41,662 (FIG. 3B), were localized in the necrotic area. In addition, other proteins were localized in the ischemic area between the necrotic center and proliferating periphery, as shown for the protein with a molecular weight of 11,639.

Example 5

Identification of Mapped Proteins

Figure 5:
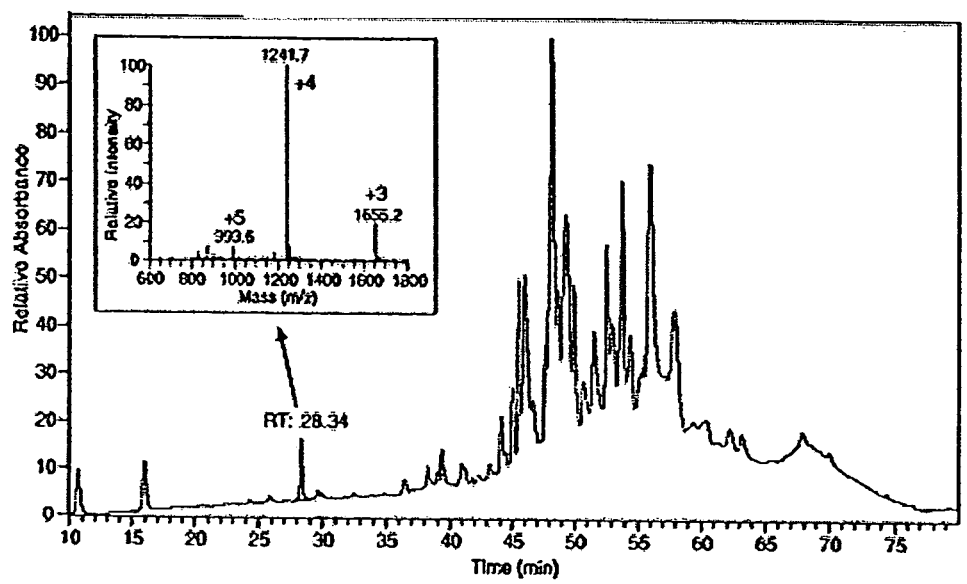
FIG. 5 shows a UV chromatogram of a LC separation on a glioblastoma xenograft extract in accordance with embodiments of the present disclosure. The analyte of molecular weight 4,964 was detected by online electrospray mass spectrometry (ESI MS) (inset shows mass spectrum) at a retention time of 28.3 min.

To identify mapped proteins, an extract of the appropriate portion of the human glioblastoma tissue was made, and then fractionated the proteins by HPLC. The UV chromatogram of such an extract is shown in FIG. 5.

Example 6

On-line Mass Spectrometric Analysis on Fraction Containing Proteins of Interest On-line mass spectrometric analysis was performed using electrospray ionization (ESI) MS (Ion Trap, Finnigan Company, San Jose, Calif.), which permitted localization of the fraction containing the proteins of interest. For example one of the proteins of molecular weight 4,964 eluted at 28.35 min in the chromatogram. The inventor and assistants spotted a sample of this fraction onto a MALDI target plate and performed an on-target digestion by trypsin. The digest was analyzed by MALDI MS followed by a database search in SwissProt using the software 'MoverZ' (ProteoMetrics, New York, N.Y.) although other software could have been used with equal results. Thymosin.4 (Tβ.4) was found to match the digest data precisely. The sequence analysis of the amino-terminal peptide performed by tandem mass spectrometry confirmed the identification of the protein as Tβ.4 in this human glioblastoma xenograft.

Increased expression of Tβ.4 has been reported in a variety of different tumors. The localization of Tβ.4 in the proliferating area of the tumor correlates with previous findings of higher levels of Tβ.4 in embryonic/neoplastic tissue compared with normal/benign tissue. One of the known activities of this immunoregulatory peptide is its ability to sequester cytoplasmic monomeric actin. Moreover, actin filaments have been shown to change into clump formation in apoptosis induced by anti-tumor drugs, a process thought to be the result of decreased Tβ.4 concentrations.

The inventor and assistants have also observed the increased expression of Tβ.4 in other tumors as well. For example, in some mouse models of prostate cancer, high levels of this protein have been found using imaging MS.

Example 7

Confirmation of Tβ.4 Protein from Mouse Prostate Tumor by Electrospray Quadrupole TOF Mass Spectrometer (ESI QTOF MS)

Figure 6:
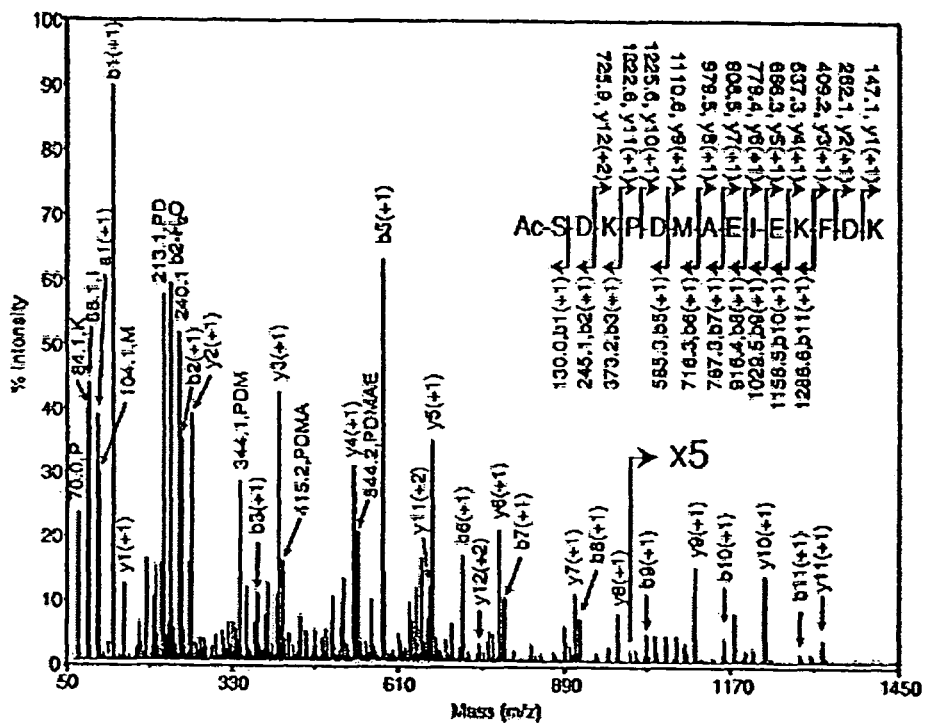
FIG. 6 shows mass spectrometric analysis by electrospray MS/MS of an N-terminal tryptic fragment of T$\beta$.4 in accordance with embodiments of the present disclosure. The complete sequence of this fragment was confirmed from mass spectrometric data.

To confirm the identification of Tβ.4, the inventor and assistants generated a fragment ion spectrum (MS/MS analysis) using an electrospray quadrupole TOF mass spectrometer (ESI QTOF MS) (Q-Star, Applied Biosystems/SCIEX, Foster City, Calif.) from one of the tryptic fragments. The MS/MS spectrum of the N-terminal tryptic peptide obtained from a similar digest of Tβ.4 purified from a mouse with prostate cancer is shown in FIG. 6. Fragment ions were matched by identifying portions of the y and b ion series, covering the complete sequence of the peptide. This spectrum confirmed the presence of Tβ.4 in mouse models of prostate cancer. Furthermore, from the MS/MS spectrum, the presence of an acetyl group at the N-terminal end of the Tβ.4 peptide was confirmed. The protein of molecular weight 11,639±2 (FIG. 3C) was similarly identified as S100 calcium-binding protein A4 (S100A4), and the protein of measured molecular weight 41,659±4 to be cytoplasmic actin.

Example 8

Tissue Preparation

Several 12 μm sections were cut from a frozen mouse brain on a Leica CM 3000 cryostat at −15° C. and directly picked up onto a gold-coated stainless steel plate. The sections were immediately transferred to a cold room (4° C.), where 10 μl of matrix (sinapinic acid, 10 mg/ml in acetonitrile/0.05% trifluoroacetic acid 50:50) were deposited with a pipette in a line adjacent to the tissue and mechanically spread over the tissue using a small plastic spatula. After air-drying for 45 min, the sections were dried for 2 h in a desiccator before mass spectrometric analysis. This application technique results in formation of crystals of the organic matrix on the surface of the tissue while minimizing the spreading of sample molecules.

Example 9

Glioblastoma Extraction and Protein Fractionation by HPLC

A portion of the glioblastoma (82 mg) was immersed in 500 μl extraction buffer (0.25 M sucrose, 0.01 M Tris-HCl and inhibitor mix; (Roche Molecular Biochemicals, Switzerland), homogenized using a Duall homogenizer and centrifuged 3 times (10 min at 680 g, 10 min at 10,000 g and 1 h at 55,000 g), each time transferring the soluble fraction to a new tube. The final fraction (50 μl) was separated over a C4 microbore column (Vydac, Hesperia, Calif.), samples were collected and the separation run was recorded with a UV detector set at 214 nm. Solvent A was 0.1% trifluoro acetic acid and solvent B was 95% acetonitrile, 4.9% water and 0.1% trifluoro acetic acid. A flow rate of 200 μl/min was used with a gradient of 5 min at 5% B, then in 55 min to 60% B, then in 10 min to 100% B, and finally 5 min at 100% B.

Example 10

On-Target Digestion by Trypsin

For this procedure, the sample (2 μl) was placed on the target and allowed to dry before adding digest solution (2 μl, 20 nM bovine trypsin, sequencing-grade, (Roche Molecular Biochemicals), and 50 mM ammonium hydrogen carbonate). The plate was kept at 37° C. for 30 min while adding water to maintain the volume. After drying the sample, 2 μl of a saturated α-cyano-4-hydroycinnamic acid (Sigma) solution in 50:50 acetonitrile and 0.1% trifluoro acetic acid (2 μl) was added as a MALDI matrix.

All of the apparatuses and methods disclosed and claimed herein can be made and executed without undue experimentation in light of the present disclosure. While techniques of this invention have been described in terms of specific embodiments, it will be apparent to those of skill in the art that variations may be applied without departing from the concept, spirit and scope of the invention. For example, as will be recognized by those of ordinary skill in the art, embodiments of this disclosure may be used in conjunction with lasers of any type, operating at any wavelength. For instance, wavelengths between about 10 and about $10^6$ Angstroms are contemplated, but this disclosure is not limited thereto. Further, the techniques described herein may be applied to any variety of samples including but not limited to samples that are not frozen, samples that are on a substrate polymer or wax (or other material), or samples embedded in a polymer or wax (or other material). All variations apparent to those skilled in the art are deemed to be within the spirit, scope and concept of the invention as defined by the appended claims.

REFERENCES

The following references are specifically incorporated herein by reference:
1. U.S. Pat. No. 5,808,300
2. U.S. Pat. No. 5,827,190
3. U.S. Pat. No. 6,225,047 B1
4. World Patent Ref. WO 00/11208 A1
5. World Patent Ref. WO 01/36977 A2
6. Caprioli, R. M., Chaeurand, P., Hallahan, D. E., & Stoeckli, M. Imaging mass spectrometry: A new technology for the analysis of protein expression in mammalian tissues. *Nature Medicine* 7, 493-496 (2001).
7. Caprioli, R. M., Farmer, T. B. & Gile, J. Molecular imaging of biological samples: Localization of peptides and proteins using MALDI-TOF MS. *Anal. Chem.* 69, 4751-4760 (1997).
8. Chaurand, P., Stoeckli, M. & Caprioli, R. M. Direct profiling of proteins in biological tissue sections by MALDI mass spectrometry. *Anal. Chem.* 71, 5263-5270 (1999).
9. Cheng, L., Neumann, R. M., Weaver, A. L., Spotts, B. E. & Bostwick, D. G. Predicting cancer progression in patients with stage T1 bladder carcinoma. *J. Clin. Oncol.* 17, 3182-3187 (1999).
10. Chong, B. E., Lubman, D. M., Miller, F. R. & Rosenspire, A. J. Rapid screening of protein profiles of human breast cancer cell lines using non-porous reverse-phase high performance liquid chromatography separation with matrix-assisted laser desorption/ionization time-of-flight mass spectral analysis. *Rapid Commun. Mass Spectrom.* 13, 1808-1812 (1999).
11. Firlik, K. S., Martinez, A. J. & Lunsford, L. D. Use of cytological preparations for the intra-operative diagnosis of stereotactically obtained brain biopsies: A 19-year experience and survey of neuropathologists. *J. Neurosurg.* 91, 454-458 (1999).
12. Gibbs, J. F., Huang, P. P., Zhang, P. J., Kraybill, W. G. & Cheney, R. Accuracy of pathologic techniques for the diagnosis of metastatic melanoma in sentinel lymph nodes. *Ann. Surg. Oncol.* 6, 699-704 (1999).

13. Hall, A. K. Differential expression of thymosin genes in human tumors and in the developing human kidney. *Int. J. Cancer* 48, 672-677 (1991).
14. Iguchi, K. et al. Decreased thymosin β.4 in apoptosis induced by a variety of antitumor drugs. *Biochem. Pharmacol.* 57, 1105-1111 (1999).
15. Jimenez, C. R. et al. Direct mass spectrometric peptide profiling and sequencing of single neurons reveals differential peptide patterns in a small neuronal network. *Biochemistry* 37, 2070-2076 (1998).
16. Karas, M., Bachmann, D., Bahr, U. & Hillenkamp, F. Matrix-assisted ultraviolet-laser desorption of nonvolatile compounds. *Int. J. Mass Spectrom. Ion Process.* 78, 53-68 (1987).
17. Klem, D., Jacobs, H. K., Jorgensen, R., Facenda, L. S., Baker, D. A., Altimari, A. "Stereotatic breast biopsy in a community hospital setting", *Am. Surg.* 65(8): 737-740-1, 1999.
18. Levisetti, R. et aL Imaging-SIMS (secondary-ion mass-spectroscopy) studies of advanced materials. *Scanning Microsc.* 7, 1161-1172 (1993).
19. Li, K. W. et al. Direct peptide profiling by mass spectrometry of single identified neurons reveals complex neuropeptide-processing pattern. *J. Biol. Chem.* 269, 30288-30292 (1994).
20. Longacre, T. A. & Hendrickson, M. R. Diffusely infiltrative endometrial adenocarcinoma—an adenoma malignum pattern of myoinvasion. *Am. J. Surg. Pathol.* 23, 69-78 (1999).
21. Moroz, L. L., Gillette, R. & Sweedler, J. V. Single-cell analyses of nitrergic neurons in simple nervous systems. *J. Exp. Biol.* 202, 333-341 (1999).
22. Nelson, D. F., McDonald, J. V., Lapham, L. W., Quazi, R. & Rubin, P. Central nervous system tumors. in *Clinical Oncology: A Multidisciplinary Approach for Physicians and Students* (ed. Rubin, P.) 617-644 (W B Saunders, Philadelphia, 1993).
23. Pacholski, M. L. & Winograd, N. Imaging with mass spectrometry. *Chem. Rev.* 99, 2977-3005 (1999).
24. Paciucoi, R. et aL Isolation of plasminogen activator, cathepsin H, and non-specific cross-reacting antigen from SK-PC-1 pancreas cancer cells using subtractive hybridization. FEBS Lett. 385, 72-76 (1996).
25. Richter, T., Nahrig, J., Komminoth, P., Kowolik, J. & Werner, M. Protocol for ultrarapid immunostaining of frozen sections. *J. Clin. Pathol.* 52, 461-463 (1999).
26. Roepstorff, P. Proposal for a common nomenclature for sequence ions in mass spectra of peptides. *Biomed. Mass Spectrom.* 11, 601 (1984).
27. Shah, A. B., Muzumdar, G. A., Chitale, A. R. & Bhagwati, S. N. Squash preparation and frozen section in intra-operative diagnosis of central nervous system tumors. *Acta Cytologica* 42, 1149-1154 (1998).
28. Silbergeld, D. L. & Chicoine, M. R. Isolation and characterization of human malignant glioma cells from histologically normal brain. *J. Neurosurg.* 86, 525-531 (1997).
29. Stoeckli, M., Farmer, T. B. & Caprioli, R. M. Automated mass spectrometry imaging with a matrix-assisted laser desorption ionization time-of-flight instrument. *J. Am. Soc. Mass Spectrom.* 10, 67-71 (1999).
30. Stryer, L., Berg, J. M., Tymoczko, J. L. Biochemistry 5$^{th}$ ed., W. H. Freeman & Co., 2002.
31. Sun, H. Q., Kwiatowska, K. & Yin, H. L. Actin monomer binding proteins. *Curr. Opin. Cell Biol.* 7, 102-110 (1995).
32. Thebauit, S., Gilbert, D., Machour, N., Marvin, L., Lange, C., Tron, F. & Charllonat, R. Two-dimensional electrophresis and mass spectrometry identification of proteins bound by a murine monoclonal anti-cardiolipin antibody: A powerfill technique to characterize the cross-reactivity of a single autoantibody. *Electrophoresis* 21, 2531-2539 (2000).
33. Todd, P. J., McMahon, J. M., Short, R. T. & McCandlish, C. A. Organic SIMS of biological tissue. *Anal. Chem.* 69, 529A-535A (1997).
34. Turner, R. R., Hansen, N. M., Stern, S. L. & Giuliano, A. E. Intra-operative examination of the sentinel lymph node for breast carcinoma staging. *Am. J. Clin. Pathol.* 112, 627-634 (1999).
35. Valaskovic, G. A. & Morrison, G. H. Quantitative imaging ion microscopy—a short review. *Scanning Microscopy* 6, 305-318 (1992).
36. Vlahou, A., Schellhammer, P. F., Mendrinos, S., Patel, K., Kondylis, F. I., Gong, L., Nasim, S. & Wright, G. L. Jr., Development of a novel proteomic approach for the detection of transitional cell carcinoma of the bladder in urine. *American Journal of Pathology.* 158, 1491-1502 (2001).
37. Wang, H. W., Willis, J., Canto, M. I. F., Sivak, M. V. & Izatt, J. A. Quantitative laser scanning confocal autofluorescence microscopy of normal, premalignant, and malignant colonic tissues. *IEEE Trans. Biomed. Eng.* 46, 1246-1252 (1999).
38. Physician's Desk Reference, Medical Economics Company Inc. (Hospital/Library Version) 2002.

What is claimed is:

1. A method of assessing a state of disease or tissue development in a specimen from a subject, comprising:
   (a) generating a solid state first specimen that has not been subjected to homogenization, release of cellular components, centrifugation or cell fractionation;
   (b) subjecting a first spot of a first specimen to desorption ionization to release a first plurality of proteins;
   (c) obtaining a first set of data comprising positional information on the first spot and a mass spectrum of the first plurality of proteins;
   (d) moving the first specimen a predetermined linear distance or generating a second solid state specimen, wherein the second specimen comprises a tissue that is related to the first specimen in time or tissue type;
   (e) subjecting a second spot of the first or the second specimen to desorption ionization to release a second plurality of proteins;
   (f) obtaining a second set of data comprising positional information on the second spot and a mass spectrum of the second plurality of proteins;
   (g) comparing the first data set with the second data set and identifying protein molecular changes and positional changes between the first and second spots; and
   (h) assessing a state of a disease or tissue development in the subject based on the identified protein molecular and positional changes.

* * * * *